United States Patent [19]
Baude et al.

[11] Patent Number: 5,016,977
[45] Date of Patent: May 21, 1991

[54] OPTICAL LENS FOR CORRECTING ASTIGMATISM

[75] Inventors: Dominique Baude, Saint Ouen; Pierre Chavel, Chilly Mazarin; Denis Joyeux, Les Ulis; Jean Taboury, Sceaux, all of France

[73] Assignee: Essilor International-Compagnie Generale, Cedex, France

[21] Appl. No.: 475,159

[22] Filed: Feb. 5, 1990

[30] Foreign Application Priority Data

Feb. 6, 1989 [FR] France .................. 89 01472

[51] Int. Cl.$^5$ .................. G02B 5/18; G02C 7/02; G02C 7/04; A61F 2/16
[52] U.S. Cl. .................. 350/162.17; 350/162.2; 350/162.21; 350/162.22; 351/160 R; 351/176; 623/6
[58] Field of Search .................. 351/160 R, 160 H, 161, 351/162, 176; 350/162.17, 162.20, 162.21, 162.22, 162.23, 162.24; 623/6

[56] References Cited

U.S. PATENT DOCUMENTS

| | | | |
|---|---|---|---|
| 3,973,850 | 8/1976 | Pouey | 350/3.7 |
| 3,985,443 | 10/1976 | Danielsson et al. | 350/162.21 |
| 4,508,436 | 4/1985 | Sitterle | 351/160 H |
| 4,641,934 | 2/1987 | Freeman | 351/160 R X |
| 4,642,112 | 2/1987 | Freeman | 351/160 R X |
| 4,655,565 | 4/1987 | Freeman | 351/161 X |
| 4,932,970 | 6/1990 | Portney | 351/160 R X |

*Primary Examiner*—Scott J. Sugarman
*Attorney, Agent, or Firm*—Blakely, Sokoloff, Taylor & Zafman

[57] ABSTRACT

The present invention relates to an optical lens for correcting astigmatism. It includes diffractive components whose outlines are delimited by conic section curves having non-degenerate centers. More precisely, in accordance with the invention, the lens includes adjacent diffractive components having hyperbolic or elliptical outlines with a periodicity in $r^2$ in two mutually orthogonal directions x and y intersecting on the axis of the lens and coinciding with the main axes of the hyperbolas or of the ellipses, which are determined respectively by the equations: $\Delta r_x^2 = 2\lambda|f_x|$; and $\Delta r_y^2 = 2\lambda|f_y|$; in which: $\Delta r_x^2$ represents the periodicity in $r^2$ along the x direction; $\Delta r_y^2$ represents the periodicity in $r^2$ along the y direction; $\lambda$ represents the mean utilization wavelength; $f_x$ represents the desired focal length in the X direction; and $f_y$ represents the desired focal length in the Y direction.

7 Claims, 8 Drawing Sheets

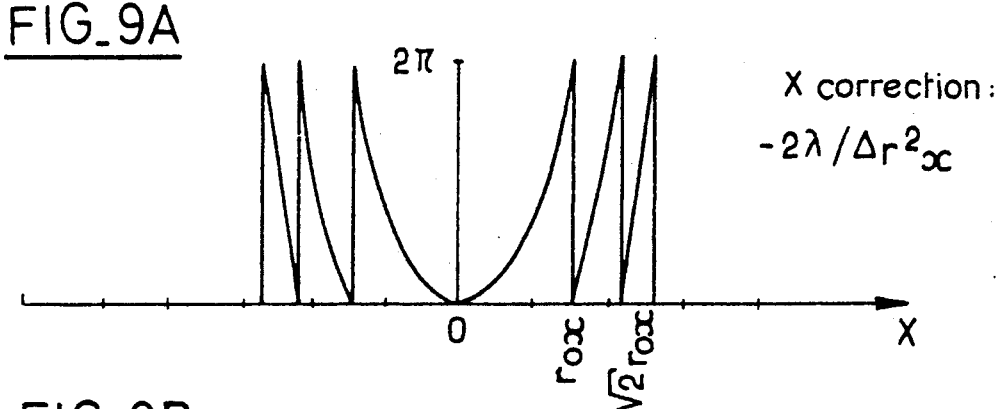
FIG._9A
X correction: $-2\lambda/\Delta r^2_x$
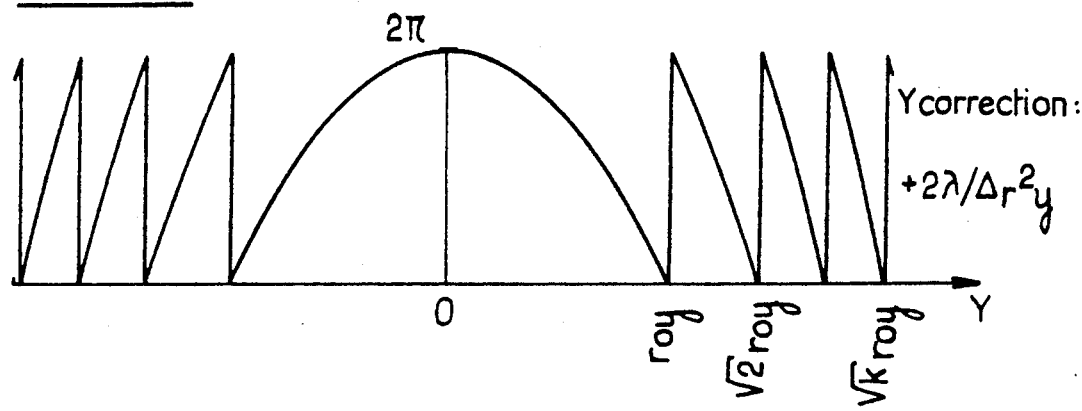
FIG._9B
Y correction: $+2\lambda/\Delta r^2_y$
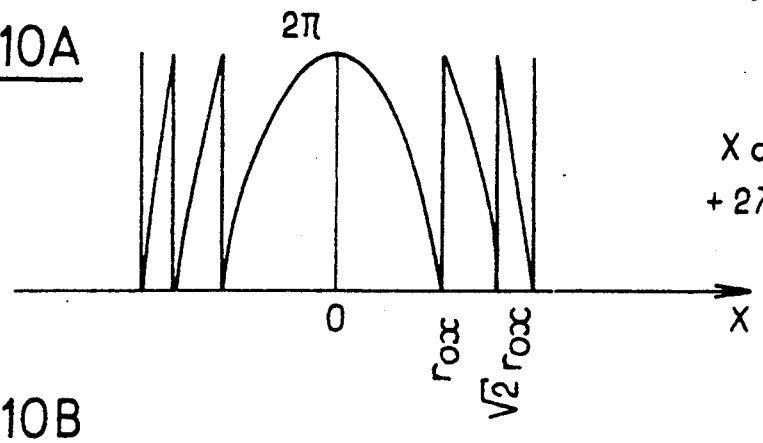
FIG._10A
X correction: $+2\lambda/\Delta r^2_x$
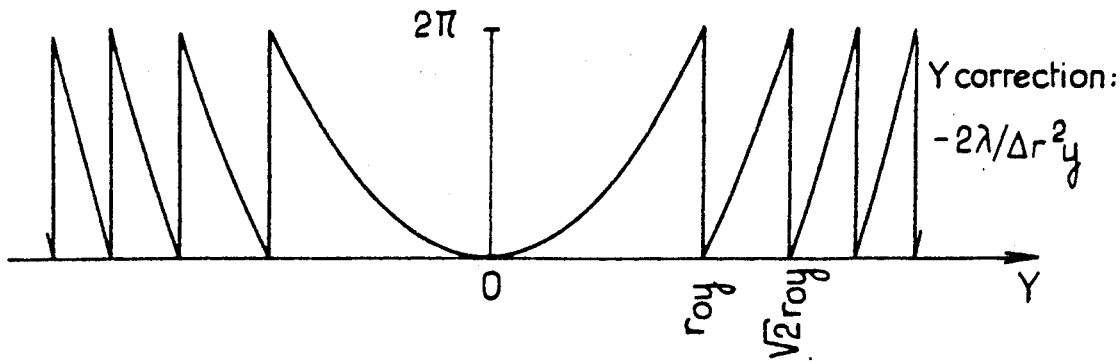
FIG._10B
Y correction: $-2\lambda/\Delta r^2_y$

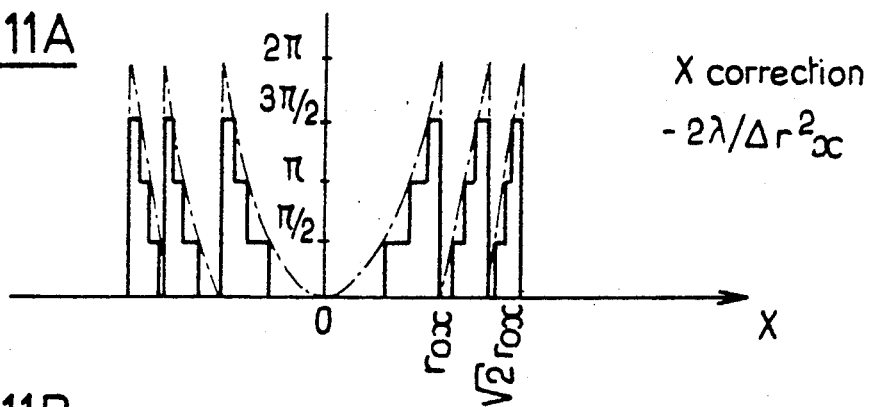
FIG_11A
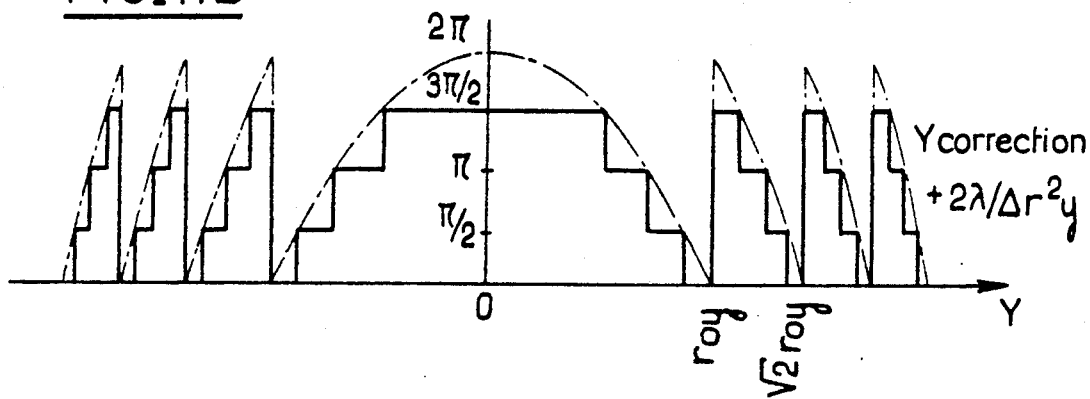
FIG_11B
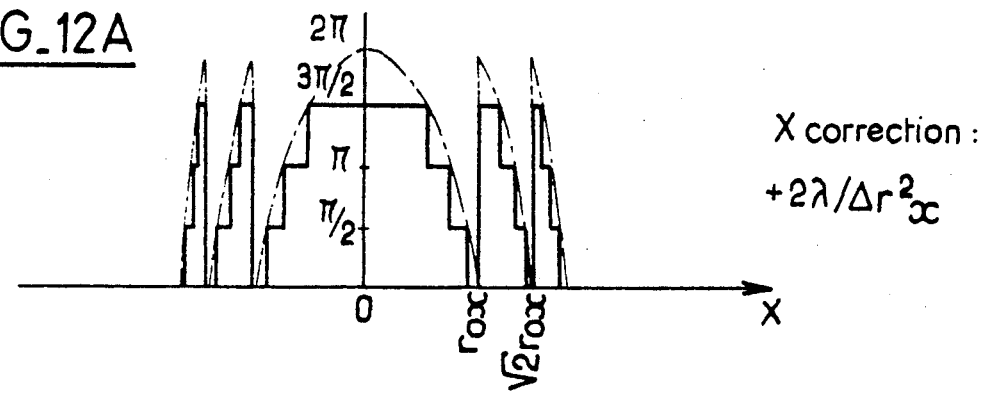
FIG_12A
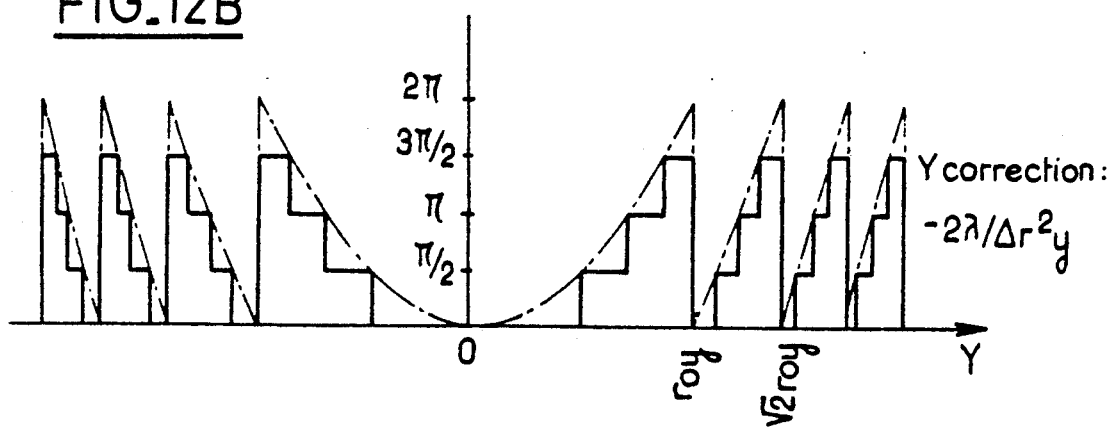
FIG_12B

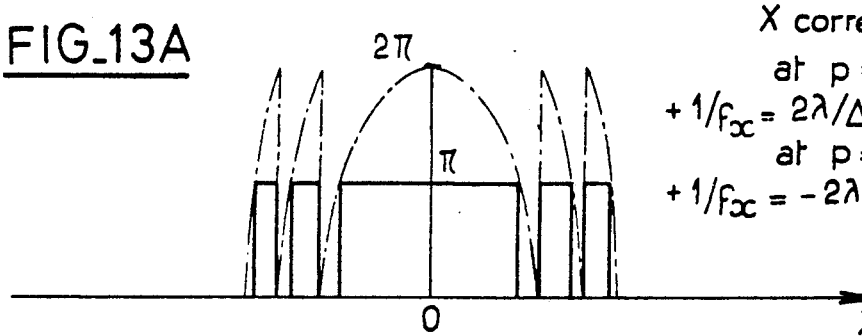
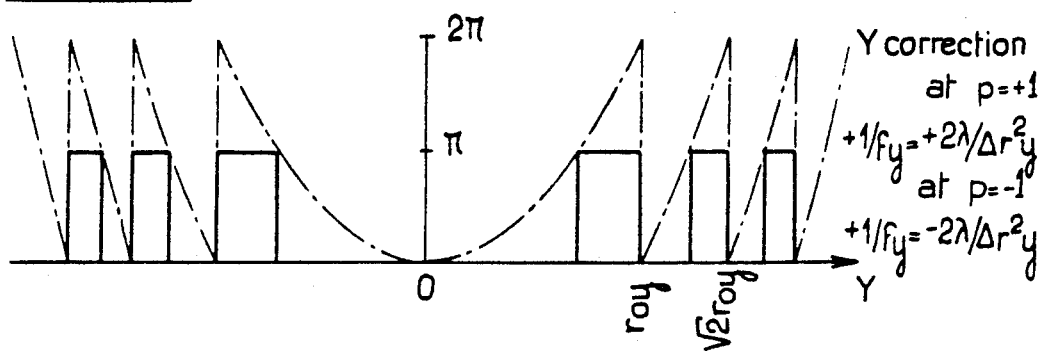
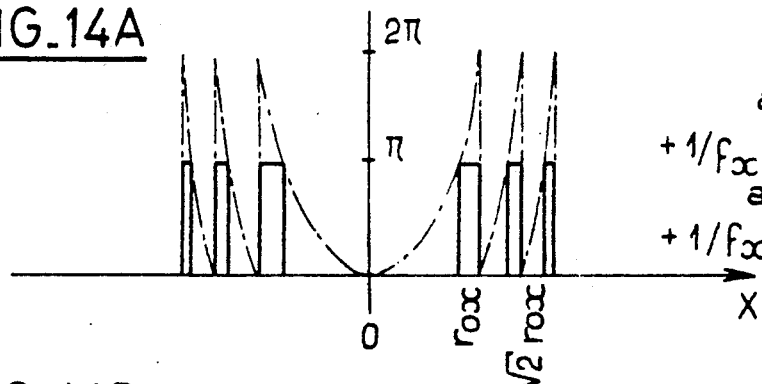
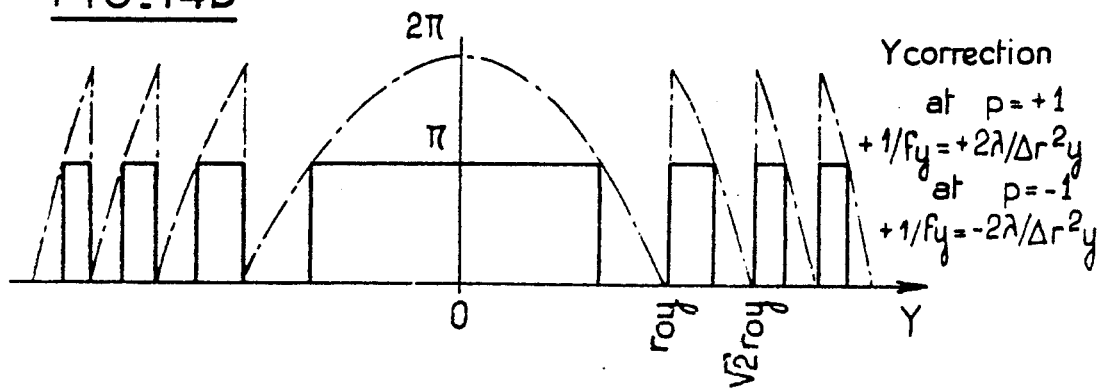

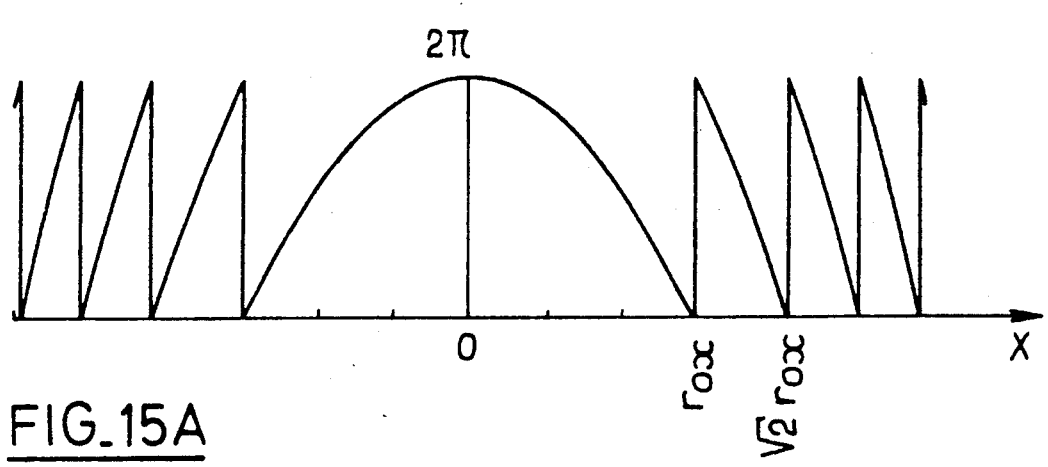
FIG._15A
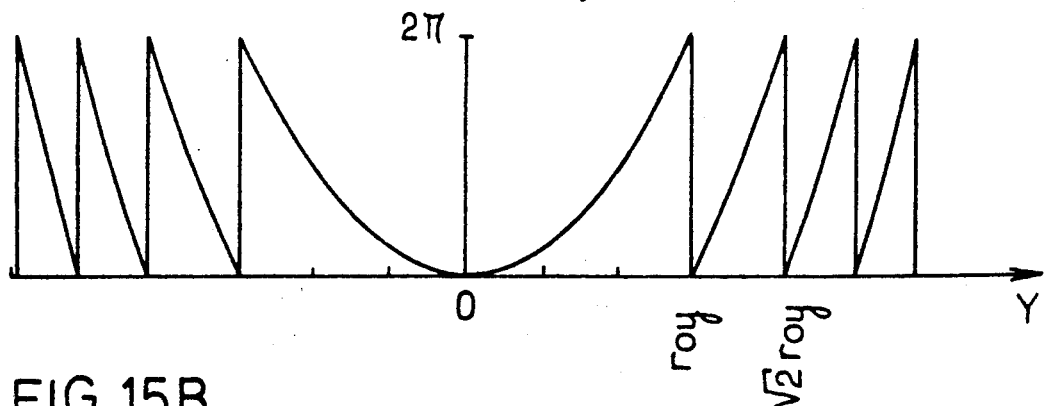
FIG._15B

OPTICAL LENS FOR CORRECTING ASTIGMATISM

The present invention relates to an optical lens for correcting astigmatism.

The lens may be a contact lens, an intra-ocular implant, or an intra-corneal lens.

BACKGROUND OF THE INVENTION

Astigmatism is a defect of the eye wich has the consequence of causing a point source situated at infinity to give rise to an image comprising two small perpendicular segments of light which are spaced apart from each other along the optical axis by a distance which is a function of the degree of astigmatism. These two segments correspond to the focal lengths of the astigmatic beam and they may be situated on the same side of the retina, either in front of it (myopic astigmatism) or behind it (hyperopic astigmatism), or else they may be situated on either side of the retina (combined astigmatism). There are two possible sources for such defects: either the cornea or else the lens of the eye; with the cornea and the lens having surfaces which are not surfaces of revolution, and which have two main radii.

Astigmatism of the eye is corrected by compensating for said aberration so that a point object gives rise to a spherical wave centered on an image point on the retina.

In the past, this correction has been obtained using sphero-cylindrical lenses which correspond functionally to associating a spherical lens with a cylindrical lens.

Such lenses have already provided good service. However, accurately defining sphero-cylindrical surfaces suitable for obtaining optimum correction is often difficult and complex.

For several years, the person skilled in the art has been considering developing presbyopia-compensating lenses comprising diffractive components (see for example European patent EP-A-0 064 812, U.S. Pat. No. 4,637,697, or French patent applications FR-88 06 699 filed May 19, 1988 and FR-88 14 634, filed Nov. 9, 1988, in the name of the present Applicant).

To this end, diffractive lenses proposed so far comprise a series of diffractive structures disposed concentrically around the optical axis of the lens.

The present invention now seeks to propose novel means for correcting astigmatism of the eye by utilizing diffractive components.

SUMMARY OF THE INVENTION

To this end, optical lenses of the present invention comprises diffractive components whose outlines are delimited by conic section curves having non-degenerate centers.

In the context of the present patent application, the term "outline" designates the frontier between two adjacent diffractive zones.

More precisely, according to the invention, the lens advantageously comprises a set of adjacent diffractive zones having hyperbolic or elliptical outlines with a periodicity in $r^2$ in two mutually orthogonal directions X and Y which are centered on the axis of the lens and which coincide with the main axes of the hyperbolas or the ellipses, with the respective periodicities being determined by the following equations:

$$\Delta r_x^2 = 2\lambda |f_x|$$

$$\Delta r_y^2 = 2\lambda |f_y|$$

in which:

$\Delta r_x^2$ represents the periodicity in $r^2$ of the diffractive components in the X plane (difference between the (n+1)-th radius and the n-th radius in the X direction);

$\Delta r_y^2$ represents the periodicity in $r^2$ of the diffractive components in the Y plane (difference between the (n+1)-th radius and the n-th radius in the Y direction);

$\lambda$ represents the mean utilization or "design" wavelength;

$f_x$ represents the desired focal length in the X direction; and $f_y$ represents the desired focal length in the Y direction.

The Applicant has determined that such a lens provided with a diffractive structure is capable of providing the same correction for astigmatism as a conventional sphero-cylindrical lens.

BRIEF DESCRIPTION OF THE DRAWINGS

Embodiments of the invention are described by way of example with reference to the accompanying drawings, in which:

FIGS. 9A and 9B show the phase profiles in two mutually orthogonal main directions X and Y of hyperbolic-outline diffractive components in accordance with the present invention; and FIGS. 10A and 10B, 11A and 11B, 12A and 12B, 13A and 13B, 14A and 14B, and 15A and 15B are respective pairs of views similar to FIGS. 9A and 9B showing other variant embodiments of hyperbolic-outline diffractive components in accordance with the present invention.

DETAILED DESCRIPTION

As mentioned above, proposals have already been made for compensating presbyopia by means of diffractive lenses comprising a series of concentric diffractive structures which are in the form of a circular rings around the optical axis of the lens.

These diffractive structures generally all have the same profile. They possess radial periodicity which defines a set of potentially available focal lengths in accordance with the equation:

$$f_p = r_0^2 / 2p\lambda$$

where:

$r_o^2$ represents the outside radius of the central structure;

p represents the order of diffraction; and

λ represents the mean utilization wavelength.

The effectiveness of different diffraction orders is determined by the phase profile of each structure.

For a diffractive component of the pure kinoform type with continuous phase variation between 0 and $2\pi$ at the design wavelength, energy is diffracted in one order only, either the order +1 or else the order −1.

For a diffractive component of the samples kinoform type having n subzones at phase differences of $2\pi/n$, diffraction order p = +1 or p = −1 is the most intense. When n = 4, diffraction efficiency at order p = +1 or p = −1 is equal to 0.81 at the design wavelength, and is equal to zero for orders 0 and −1 or +1, while the remaining energy is distributed over higher orders.

For a diffractive component having a binary profile comprising two subzones at a phase difference of $\pi$, diffraction order p = +1 and p = −1 are the most intense, each diffracting 41% of the incident energy, with order 0 being extinguished at the design wavelength.

Whereas the diffractive lenses proposed in the past for compensating presbyopia have diffractive structures in the form of circular rings about the optical axis of the lens, a lens in accordance with the present invention has adjacent diffractive structures whose outlines are not circular about the optical axis, but are delimited by conic section curves being non-degenerates centers.

Figure 1:
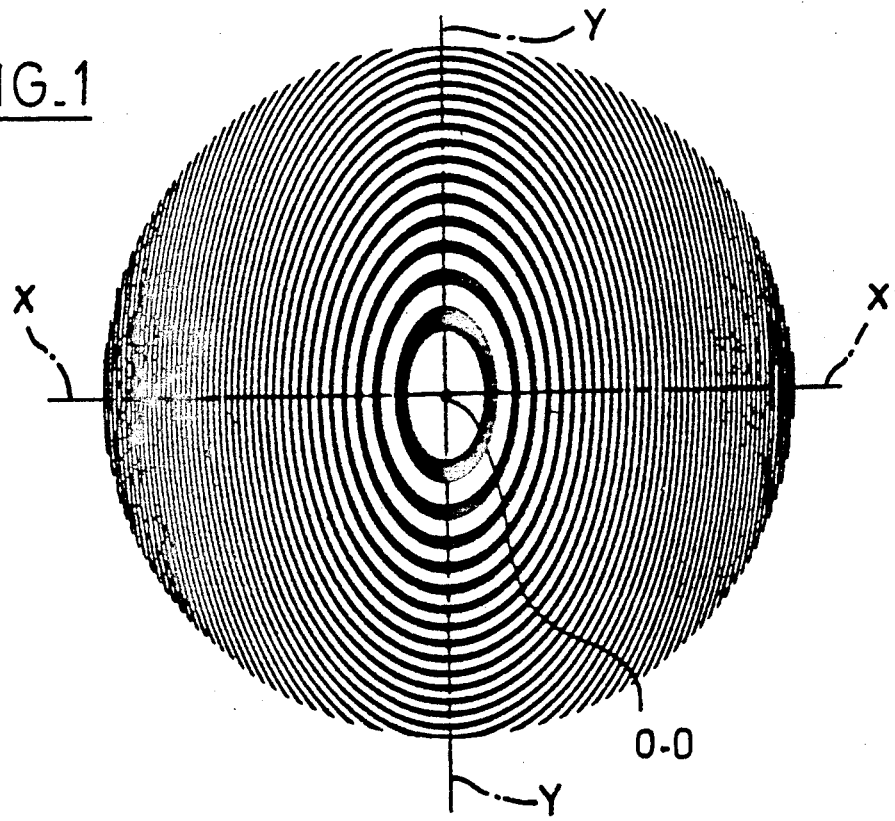
FIG. 1 is a diagrammatic plan view in a plane orthogonal to the optical axis O—O of the lens showing the distribution of elliptical-outline diffractive zones describing the diffractive components of an optical lens in accordance with the present invention.
Figure 2:
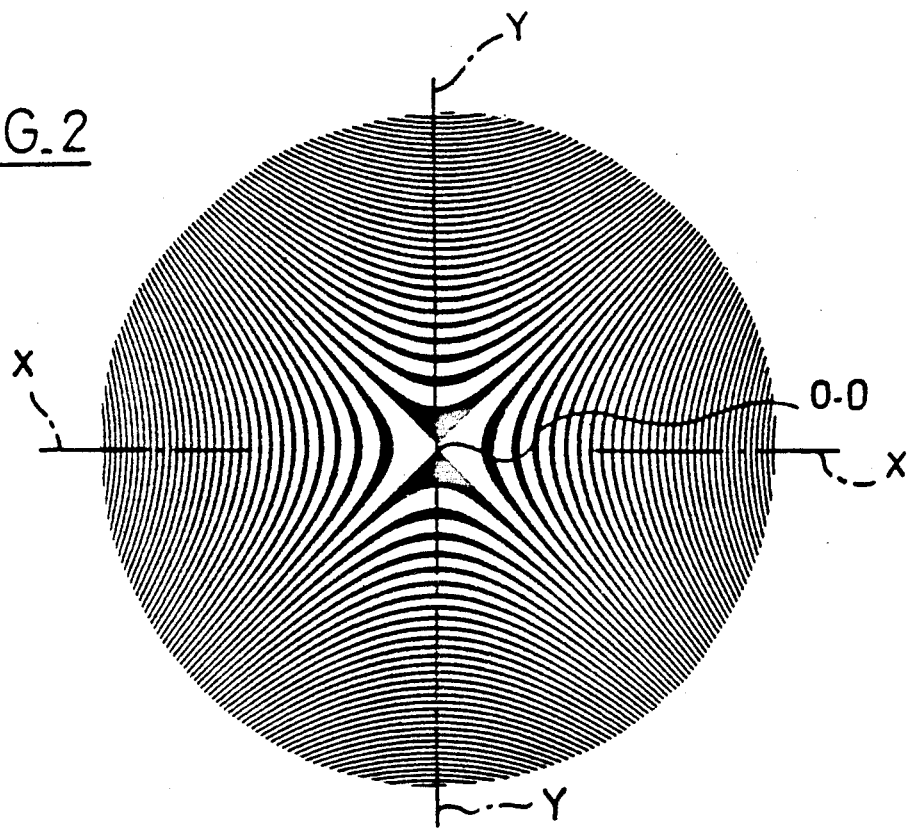
FIG. 2 is a similar diagrammatic plan view on a plane orthogonal to the optical axis O—O of the lens showing the distribution of hyperbolic-outline diffractive zones describing the diffractive components of another lens in accordance with the present invention.

More precisely, in accordance with the invention, adjacent diffractive zones are advantageously elliptical or hyperbolic in outline as shown in FIGS. 1 and 2 respectively.

These FIGS. 1 and 2 are given views of lenses in accordance with the present invention having diffractive components which are elliptical or hyperbolic in outline. That is to say that the axis O—O of each of the lenses is perpendicular to the plane of FIGS. 1 and 2.

These figures are diagrammatic. The alternating light and dark regions in FIGS. 1 and 2 illustrate the periodicity of alternating diffractive structures in accordance with the invention, with a diffraction zone in this scheme being constituted by a light region and an adjacent dark region.

In the following description, the two mutually-orthogonal main directions intersecting on the axis O—O of the lens are called X and Y, and they coincide with respective ones of the two orthogonal directions for which the eye has two different focal lengths. In addition, the two focal lengths of a lens in accordance with the present invention in said two directions are called $f_x$ and $f_y$.

Initially, the description provides greater detail concerning lenses of the present invention having elliptical outline diffractive components of the type shown in FIG. 1.

The equation of the boundary between two adjacent elliptical-outline diffractive zones as shown in FIG. 1 is given by the equation:

$$x^2/|f_x| + y^2/|f_y| = 2\lambda k$$

where k represents an integer.

The excentricity of the elliptical curves defined in this way depends on the difference between the absolute values of the focal lengths $f_x$ and $f_y$.

The elliptical-outline diffractive components are symmetrical simultaneously about each of the directions X and Y, which directions coincide with the main axes of the elliptical curves.

The periodicity in $r^2$ in the X direction of the elliptical-outline diffractive components is: $\Delta r_x^2 = 2\lambda |f_x|$.

The periodicity in $r^2$ in the Y direction of the elliptical-outline diffractive components is: $\Delta r_y^2 = 2\lambda |f_y|$.

The elliptical outline diffractive components may have a phase profile of the pure kinoform type, of the samples kinoform type, or a squarewave function type at 0, $\pi$, etc. In addition, the phase profile $\phi$ for each zones may be an increasing function or a decreasing function of r. Also, the variation law used (pure or samples kinoform, squarewave) may vary from one zone to another.

The absolute value of the correction power obtained in the directions X and y depends on the respective periodicities $\Delta r_x^2$ and $\Delta r_y^2$. The absolute value of the correction power in the X direction is $2\lambda/\Delta r_x^2$ for diffraction order +1 or −1, and in the Y direction is it $2\lambda/\Delta r_o^2$.

The sign of the correction provided depends both on the diffraction order and on the sign of $d\phi/dr$.

For elliptical-outline diffractive components having a phase profile of the pure kinoform or of the samples kinoform type with $d\phi/dr$ positive, the correction provided by these components is either solely or mainly at order −1, and this correction is negative, whereas when $d\phi/dr$ is negative, these components provide correction solely or mainly at order +1 and the correction is positive.

For elliptical-outline diffractive components having a phase profile of the 0, $\pi$ squarewave function type, the correction provided is positive at order +1 and negative at order −1.

FIGS. 3A and 3B, 4A and 4B, 5A and 5B, 6A and 6B, 7A and 7B, and 8A and 8B are respective pairs of X and Y phase profiles for six elliptical-outline diffractive components in accordance with the present invention.

Figure 3A:
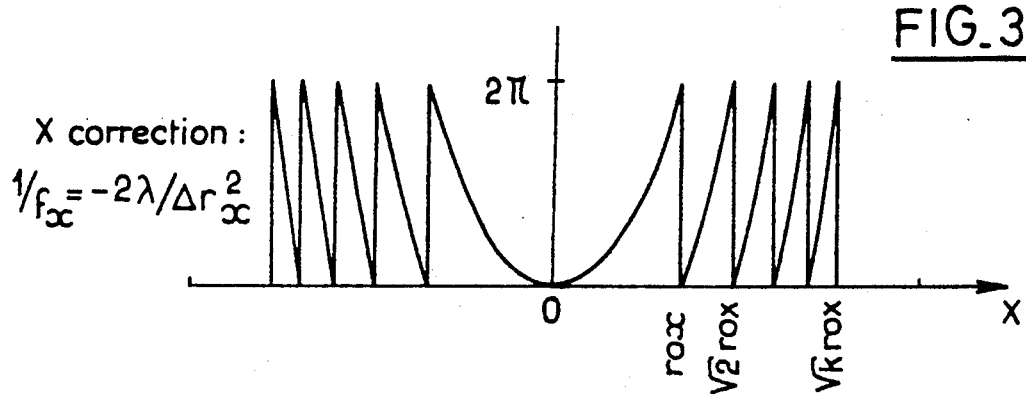
FIGS. 3A and 3B show the phase profiles in two mutually orthogonal main directions X and Y of elliptical-outline diffractive components in accordance with the present invention.
Figure 3B:
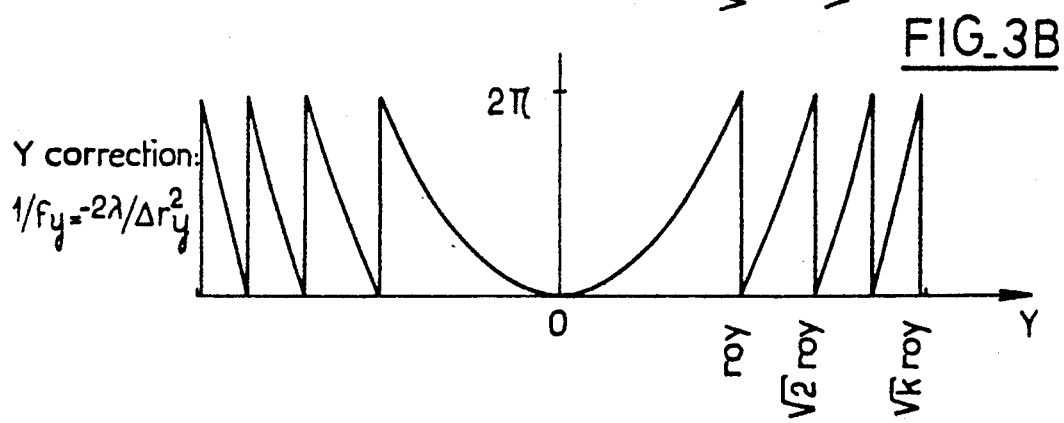

In FIGS. 3A and 3B, the phase profiles of the elliptical-outline diffractive components are of the pure kinoform type with phase varying from 0 to $2\pi$ going away from the optical axis O—O in accordance with a law which is linear in $r^2$. The diffraction components whose phase profiles are shown in FIGS. 3A and 3B operate solely in order p = −1 at the design wavelength. They provide the following correction powers in the directions X and Y respectively:

$$+1/f_x = -2\lambda/\Delta r_x^2$$

$$+1/f_y = -2\lambda/\Delta r_y^2$$

Lenses equipped with diffractive components having the phase profiles shown in FIGS. 3A and 3B therefore correct only one ametropia, with a basic correction of $-2\lambda/\Delta r_x^2$ and with an astigmatism correction of $+(2\lambda/\Delta r_x^2 - 2\lambda/\Delta r_y^2)$ i.e. a cylinder having an axis parallel to X. It will be observed that this correction is equivalent to a basic correction of $-2\lambda/\Delta r_y^2$ together with an astigmatism correction of $(2\lambda/\Delta r_y^2 - 2\lambda/\Delta r_x^2)$, i.e. a cylinder having its axis parallel to Y.

Figure 4A:
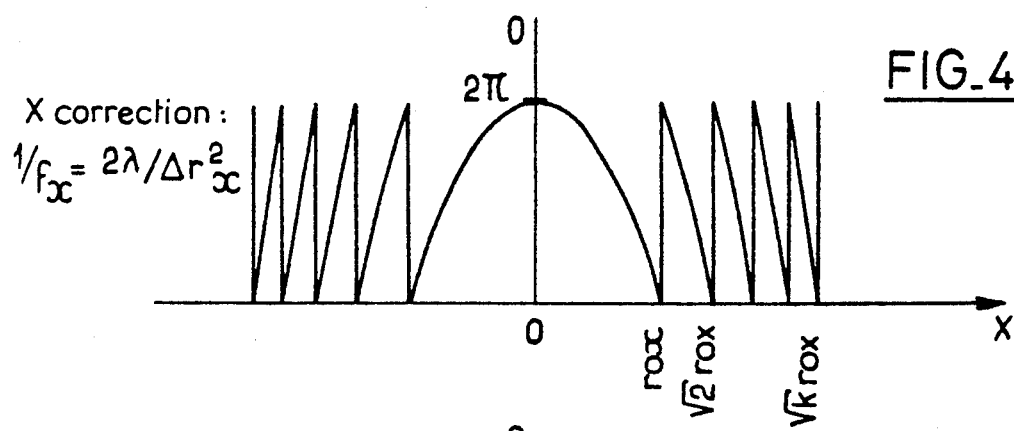
FIGS. 4A and 4B, 5A 5B, 6A and 6B, 7A and 7B, and 8A and 8B are respective pairs of figures similar to FIGS. 3A and 3B showing variant embodiments of elliptical-outline diffractive components in accordance with the present invention.
Figure 4B:
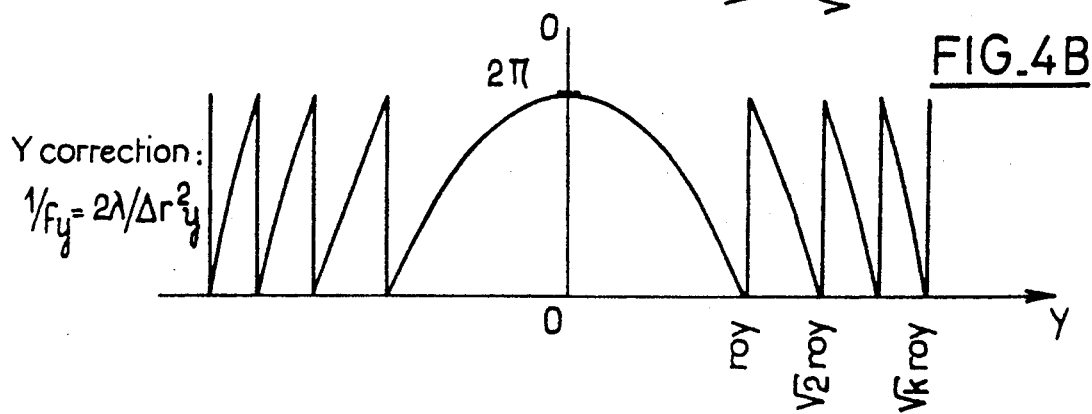

FIGS. 4A and 4B show the phase profiles of elliptical-outline diffractive components, likewise of the pure kinoform type, but in which phase varies from $2\pi$ to 0 going away from the optical axis O—O in accordance with a law which is linear in $r^2$ (i.e. in a manner which is inverse to that of FIGS. 3A and 3B). The diffractive components whose phase profiles are shown in FIGS.

4A and 4B work in order p=+1 only at the design wavelength. They provide the following correction powers in the X and Y directions respectively (with opposite signs to those mentioned above with respect to FIGS. 3A and 3B):

$$1/f_x \lambda / \Delta r_x^2$$

$$1/f_y = 2\lambda / \Delta r_y^2$$

Lenses equipped with diffractive components having the phase profiles shown in FIGS. 4A and 4B thus correct a single ametropia with a basic correction of $+2\lambda/\Delta r_y^2$ and an astigmatism correction of $+(2\lambda/\Delta r_x^2 - 2\lambda/\Delta r_y^2)$, i.e. a cylinder whose axis is parallel to Y. It will be observed that this correction is equivalent to a basic correction of $+2\lambda/\Delta r_x^2$ and an astigmatism correction of $(2\lambda/\Delta r_y^2 - 2\lambda/\Delta r_x^2)$, i.e. a cylinder having its axis parallel to X.

Figure 5A:
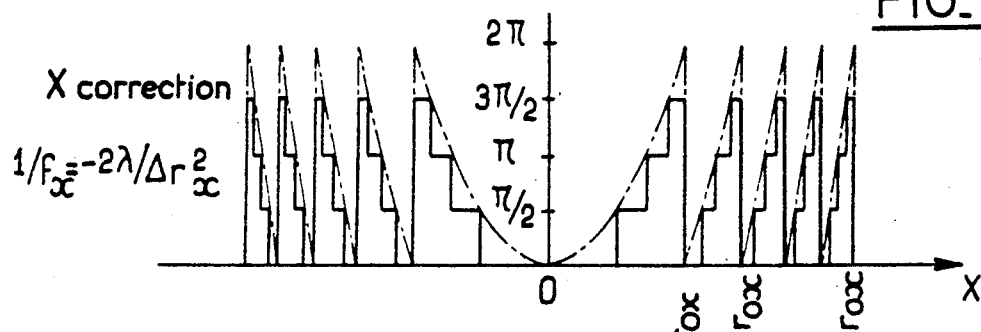
Figure 5B:
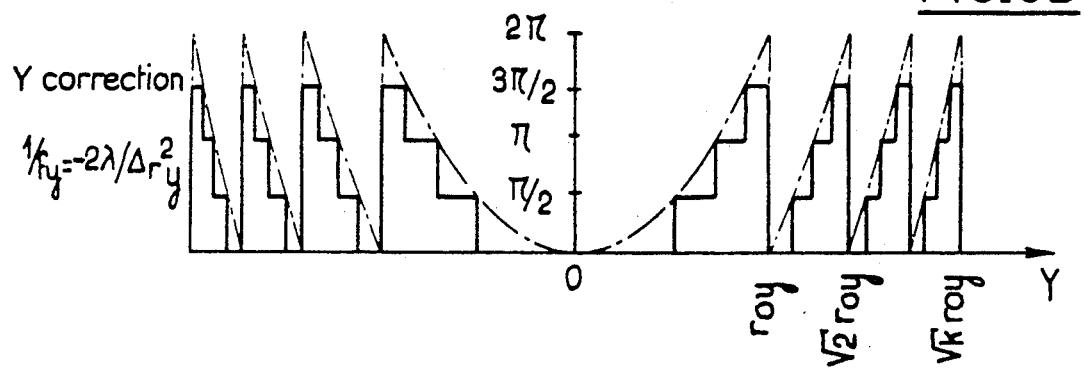

FIGS. 5A and 5B show the phase profiles of elliptical-outline diffractive components of the sample kinoform type samples in four subzones at phase intervals of $2\pi/4$, stepping through 0, $\pi/2$, $\pi$, and $3\pi/2$ going away from the optical axis O—O. The diffractive components whose phase profiles are shown in FIGS. 5A and 5B operate mainly in order p=−1 at the design wavelength. They thus provide the same correction powers and serve to correct the same ametropia as the components whose phase profiles are shown in FIGS. 3A and 3B.

Figure 6A:
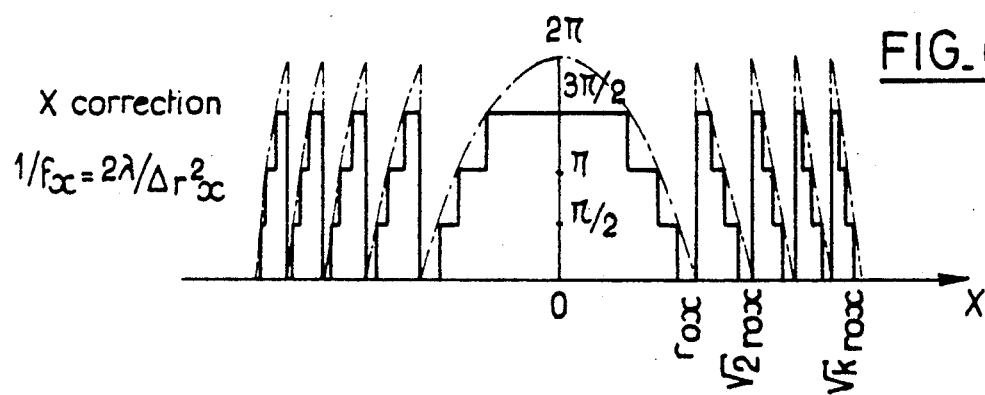
Figure 6B:
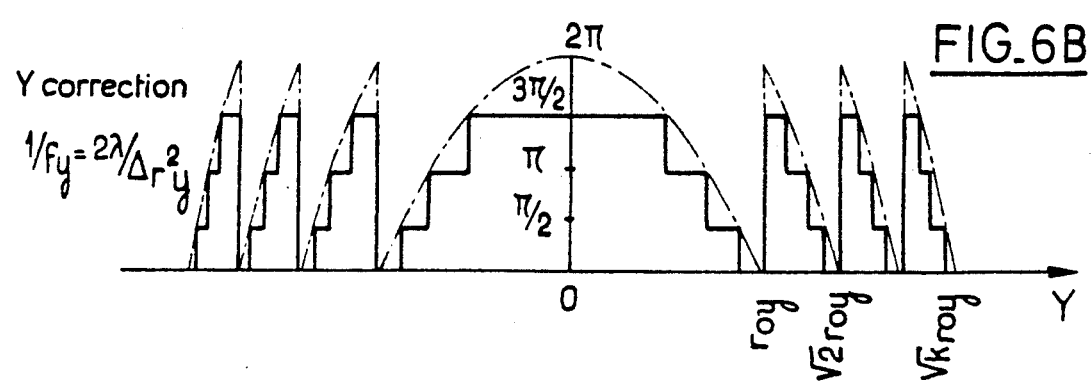

FIGS. 6A and 6B show the phase profiles of elliptical-outline diffractive components of the sampled kinoform type outline diffractive components of the sampled kinform type samples in four subzones at phase intervals of $2\pi/4$, stepping through $3\pi/2$, $\pi$, $\pi/2$, and 0 going away from the optical axis O—O. The diffractive components whose phase profiles are shown in FIGS. 6A and 6B operate mainly at order p++1 at the design wavelength. They therefore provide the same correction powers and serve to correct the same ametropia as the components whose phase profiles are shown in FIGS. 4A and 4B.

Figure 7A:
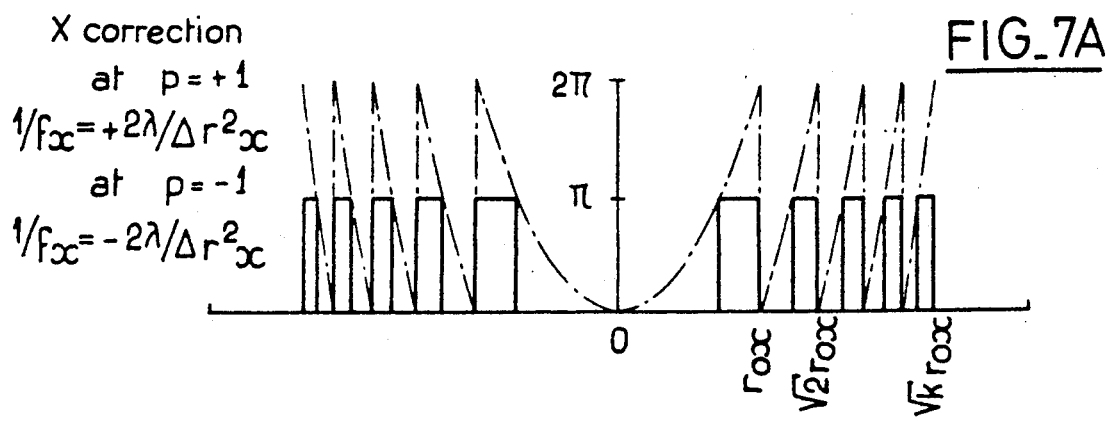
Figure 7B:
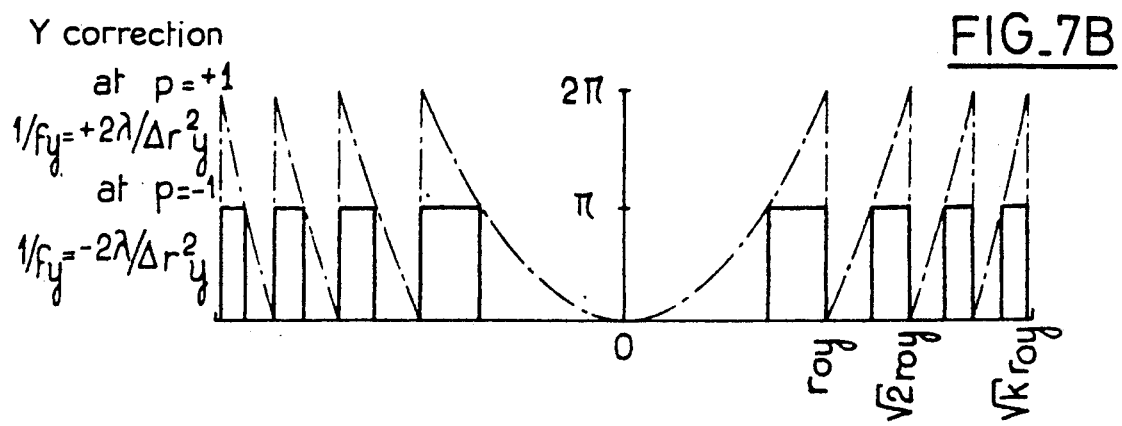

FIGS. 7A and 7B show the phase profiles of elliptical-outline diffractive components of binary profile comprising two subzones at a phase interval of $\pi$, more precisely, for each diffractive structure, there is a 0 phase shift zones close to the optical axis O—O and a $\pi$ phase shift zone at a distance from the optical axis O—O. The diffractive components whose phase profiles are shown in FIGS. 7A and 7B operate simultaneously at order p=+1 and order p=−1 at the design wavelength, with an efficiency e=0.4 in each of the orders.

At orders p=+1, they provide the following correction powers in the X and Y directions respectively:

$$+1/f_x = +2\lambda/\Delta r_x$$

and $$+1/f_y = +2\lambda/\Delta r_y^2$$

At order p=−1, the same diffractive components provide the following opposite-sign correction powers in the directions X and Y respectively, i.e.:

$$1/f_x = -2\lambda/\Delta r_x^2;$$

and $$1/f_y = -2\lambda/\Delta r_y^2$$

Lenses equipped with diffractive structures having phase profiles as illustrated in FIGS. 7A and 7B may be used for four types of correction.

At order p=+1 they provide a basic correction of $+2\lambda/\Delta r_x^2$ and an astigmatism correction of $(-2\lambda/\Delta r_x^2 + 2\lambda/\Delta r_y^2)$, i.e. a cylinder having its axis parallel to X. It may be observed that this correction is equivalent to a basic correction of $2\lambda/\Delta r_y^2$ and an astigmatism correction of $(2\lambda/\Delta r_x^2 - 2\lambda/\Delta r_y^2)$, i.e. a cylinder having its axis parallel to Y.

At order p=−1, they provide a basic correction of $-2\lambda/\Delta r_y^2$ and an astigmatism correction of $+(2\lambda/\Delta r_y^2 - 2\lambda/\Delta r_x^2)$, i.e. a cylinder having its axis parallel to Y. It may be observed that this correction is equivalent to a basic correction of $-2\lambda/\Delta r_x^2$ and an astigmatism correction of $(2\lambda/\Delta r_x^2 - 2\lambda/\Delta r_y^2)$, i.e. a cylinder having its axis parallel to X.

Two other corrections are obtained by combining the orders p=+1 and p=−1.

At orders p=+1 in the X direction and p=−1 in the Y direction, the basic correction obtained in $2\lambda/\Delta r_x^2$ and the astigmatism correction is $(-2\lambda/\Delta r_x^2 - 2\lambda/\Delta r_y^2)$, i.e. a cylinder whose axis is parallel to X. It may be observed that this correction is equivalent to a basic correction of $-2\lambda/\Delta r_y^2$ and an astigmatism correction of $(2\lambda/\Delta r_x^2 + 2\lambda/\Delta r_y^2)$, i.e. a cylinder having its axis parallel to Y.

At order p=−1 in the X direction and p==1 in the Y direction, a basic correction is obtained of $-2\lambda/\Delta r_x^2$ and an astigmatism correction of $(2\lambda/\Delta r_x^2 + 2\lambda/\Delta r_y^2)$, i.e. a cylinder having its axis parallel to X. It may be observed that this correction is equivalent to a basic correction of $+2\lambda/\Delta r_y^2$ and an astigmatism correction of $-(2\lambda/\Delta r_x^2 + 2\lambda/\Delta r_y^2)$, i.e. a cylinder having its axis parallel to Y.

Figure 8A:
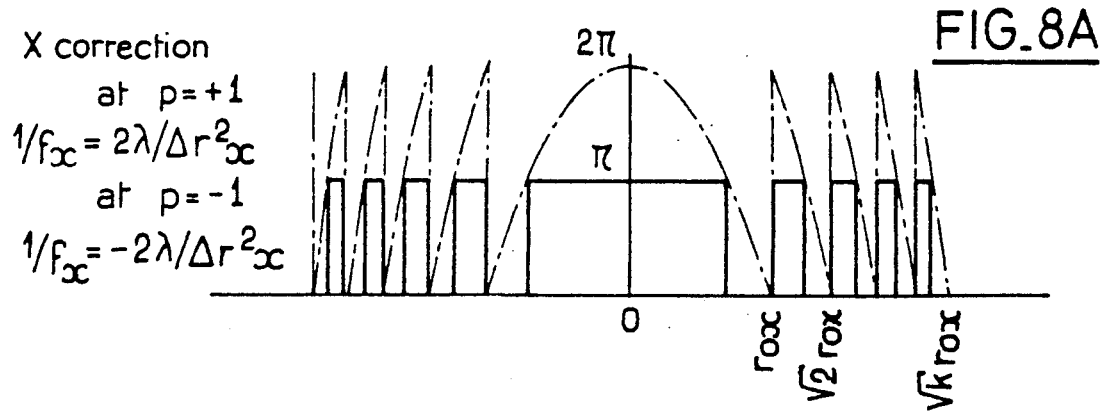
Figure 8B:
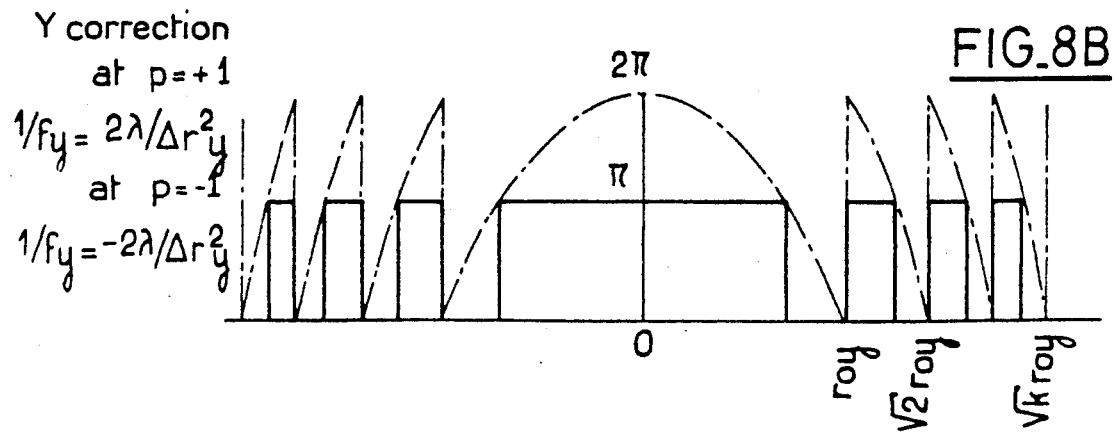

FIGS. 8A and 8B show the phase profiles of elliptical-outline diffractive components, which profiles are binary including two subzones offset by $\pi$, but this time the first subzone close to the optical axis O—O provides a phase shift of $\pi$ and the second subzone going away from the optical axis O—O provides zero phase shift.

The diffractive components whose phase profiles are shown in FIGS. 8A and 8B have the same correction powers in orders +1 and −1 as the components illustrated in FIGS. 7A and 7B.

Lenses including diffractive components as described above may have additional refractive power added thereto by virtue of lens geometry.

This additional refractive power is essential if it is desired to obtain a lens including a diffractive component which is elliptical in structure and of the pure kinoform type or the sampled kinoform type if a lens is required having corrective powers of opposite signs in the X and Y directions.

By way of example, assume that a lens includes an elliptical structure diffractive component of the pure or sampled kinoform type and that its total power in the X direction is <0 and its total power in the Y direction >0, with $P_x$ diffractive being >0 and $P_y$ diffractive >0. Then, if the refractive power of the lens is written P, it is necessary that $|P| > P_x$ diffractive in order to ensure that:

$P_{total}$ in the X direction <0; and $P_{total}$ in the Y direction >0.

Three examples of the correction obtained using elliptical-outline diffractive components are now described.

EXAMPLE 1

A correction of −4d with +2d for astigmatism (a cylinder whose axis is parallel to the X direction) may be obtained without any additional refractive power by using an ophthalmic lens of the type shown in FIGS. 3A and 3B or of the type shown in FIGS. 5A and 5B, giving rise to a diffractive power $P_x = -4d$ in the X direction and a diffractive power $P_y = -2d$ in the the direction, using a radial variation law $$r_{Kx} = \sqrt{2k\lambda |f_x|} = 0.52 \sqrt{k} \text{ mm, and}$$

$$r_{Ky} = \sqrt{2k\lambda |f_y|} = 0.74 \sqrt{k} \text{ mm.}$$

EXAMPLE 2

A correction of +2d with +2d for astigmatism (a cylinder having its axis parallel to Y) may be obtained without additional refractive power by using an ophthalmic lens of the type shown in FIGS. 4A and 4B or of the type shown in FIGS. 6A and 6B, generating a diffractive power $P_x = +4d$ in the X direction and a power $P_y = +2d$ in the Y direction i.e. having a radial variation law $$r_{Kx} = \sqrt{2k\lambda f_x} = 0.52 \sqrt{k} \text{ mm, and}$$

$$r_{Ky} = \sqrt{2k\lambda f_y} = 0.74 \sqrt{k} \text{ mm.}$$

EXAMPLE 3

The diffractive components whose phase profiles are shown in FIGS. 7A and 7B and in FIGS. 8A and 8B can be used respectively for obtaining the same X and Y corrections by using the same radial periodicity $$r_{Kx} = \sqrt{2k\lambda f_x} = 0.52 \sqrt{k} \text{ mm, and}$$

$$r_{Ky} = \sqrt{2k\lambda f_y} = 0.74 \sqrt{k} \text{ mm.}$$

Components in accordance with FIGS. 7A and 7B and FIGS. 8A and 8B having order $p = -1$ provide a basic correction of −4d with an astigmatism correction of +2d (cylinder having its axis parallel to X). In addition, the same components in accordance with FIGS. 7A and 7B and FIGS. 8A and 8B, but at order $p = +1$, provide a basic correction of +2d with an astigmatism correction of +2d (a cylinder whose axis is parallel to Y).

There now follows a more detailed description of optical lenses in accordance with the present invention and provided with hyperbolic-outline diffractive components of the type shown in FIG. 2.

The boundaries between adjacent hyperbolic-outline diffractive zones are defined by two equations:

$$x^2/|f_x| - y^2/|f_y| = 2k\lambda \text{ and}$$

$$y^2/|f_y| - x^2/|f_x| = 2k\lambda$$

in which k represents an integer.

Optical lenses provided with hyperbolic-outline diffractive components comprise two series of diffractive components whose boundaries are defined by hyperbolic curves whose focal axis coincide respectively with the X and Y axes.

The hyperbolic-outline diffractive components thus also have twofold symmetry about the X and Y axes respectively which axes coincide with the focal axes of the hyperbolic curves.

The periodicity in $r^2$ along the X axis of the hyperbolic-outline diffractive components is: $\Delta r_x^2 = 2\lambda |f_x|$.

The periodicity in $r^2$ along the Y axis of the hyperbolic-outline diffractive components is: $\Delta r_y^2 = 2\lambda |f_y|$.

The hyperbolic outline diffractive components may have a phase profile of the pure kinoform type, of the sample kinoform type, or of the squarewave function type in 0, $\pi$.

In addition, the phase profile $\phi$ may be an increasing or decreasing function of r for each zone. Likewise, the variation law used (pure or sampled kinoform, squarewave, ...) may change from one zone to another. Since the $f_x$ and $f_y$ corrections are of opposite signs for a pure or sampled kinoform type diffractive component, the directions in which the phase profiles $\phi$ vary along the X axis and along the Y axis are thus of opposite sign. $d\phi/dr_x$ and $d\phi/dr_y$ are therefore opposite in sign, and this is illustrated in FIG. 2 by the discontinuity along the asymptotes.

The absolute value of the correction power obtained in the X and Y planes depends on the respective periodicities $\Delta r_x^2$ and $\Delta r_y^2$. The correction power along the X axis has an absolute value of $2\lambda/\Delta r_x^2$ and along the Y axis has an absolute value of $2\lambda/\Delta r_y^2$.

The sign of the correction obtained depends both on the diffraction order and on the direction (increasing or decreasing when going away from the lens axis O—O) of the change in the phase profile.

For hyperbolic-outline diffractive components having a pure or samples kinoform type phase profile, the correction provided is negative when $d\phi/dr$ is positive in the direction under consideration, and the correction provided is positive when $d\phi/dr$ is negative in the direction under consideration.

For hyperbolic-outline diffractive components having a 0, $\pi$ squarewave function type phase profile, the correction provided in any direction has the same sign as the diffraction order under consideration.

FIGS. 9A and 9B, 10A and 10B, 11A and 11B, 12A and 12B, 13A and 13B, 14A and 14B, and 15A and 15B are respectively pairs of X and Y phase profiles for seven hyperbolic-outline diffractive components in accordance with the present invention.

In FIGS. 9A and 9B, the phase profiles of the hyperbolic-outline diffractive components are of the pure kinoform type with phase varying from 0 to $2\pi$ in accordance with a law that is linear in $r^2$ on going away from the optical axis O—O along the X axis, and form $2\pi$ to 0 in accordance with a law which is linear in $r^2$ on going away from the optical axis O—O along the y axis. As the design wavelength, these components operate solely at order $p = -1$ in the X direction and $p = +1$ in the Y direction. They provide the following correction powers in the X and Y directions:

$$+1/f_x = -2\lambda/\Delta r_x^2$$

$$+1/f_y = -2\lambda/\Delta r_y^2$$

Lenses equipped with diffractive components having the phase profiles shown in FIGS. 9A and 9B therefore correct a single ametropia with a basic correction of $-2\lambda/\Delta r_x^2$ and an astigmatic correction of $+(2\lambda/\Delta r_x^2+2\lambda/\Delta r_y^2)$, i.e. a cylinder having its axis parallel to X. It may be observed that this correction is equivalent to a basic correction of $+2\lambda/\Delta r_y^2$ and an astigmatic correction of $-(2\lambda/\Delta r_x^2+2\lambda/\Delta r_y^2)$, i.e. a cylinder having its axis parallel to Y.

In FIGS. 10A and 10B, the phase profiles of hyperbolic-outline diffractive components are of the pure kinoform type with phase varying from $2\pi$ to 0 in accordance with a law which is linear in $r^2$ on going away from the optical axis O—O along the X axis, and from 0 to $2\pi$ in accordance with a law which is linear in $r^2$ on going away from the optical axis O—O along the Y axis. At the design wavelength, these components operate solely at order $p=+1$ in the X direction and at order $p=-1$ in the Y direction. They provide the following correction powers in the X and Y directions respectively:

$+1/f_x=+2\lambda/\Delta r_x^2$ $+1/f_y=-2\lambda/\Delta r_y^2$

Lenses equipped with diffractive components having phase profiles as shown in FIGS. 10A and 10B thus correct a single ametropia having a basic correction of $-2\lambda/\Delta r_y^2$ and an astigmatic correction of $+(2\lambda/\Delta r_x^2+2\lambda/\Delta r_y^2)$, i.e. a cylinder having its axis parallel to Y. It may be observed that this correction is equivalent to a basic correction of $+2\lambda/\Delta r_x^2$ and an astigmatic correction of $-(2\lambda/\Delta r_x^2+2\lambda/\Delta r_y^2)$, i.e. a cylinder having its axis parallel to Y.

In FIGS. 11A and 11B, the phase profiles of the hyberbolic outline diffractive components are of the sampled kinoform type having four zones at phase differences of $2\pi/4$ with phase increasing from 0 through $\pi/2$, $\pi$, $3\pi/2$ going away from the optical axis O—O along the X axis, and decreasing from $3\pi/2$, through $\pi$, $\pi/2$ and 0 going away from the optical axis O—O along the Y axis. At the design wavelength, these components operate mainly at order $p=-1$ in the X direction and $p=+1$ in the Y direction. They provide the same correction powers in the X and Y directions respectively as the components shown in FIGS. 9A and 9B:

$+1/f_x=-2\lambda/\Delta r_x^2$ $+1/f_y=+2\lambda/\Delta r_y^2$

Lenses equipped with diffractive components having phase profiles as shown in FIGS. 11A and 11B therefore correct the same ametropia as the lenses shown in FIGS. 9A and 9B.

In FIGS. 12A and 12B, the phase profiles of the hyperbolic-outline diffractive components are of the sampled kinoform type having four subzones at phase differences of $2\pi/4$, with phase decreasing through steps of $3\pi/2$, $\pi$, $\pi/2$, and 0 going away from the optical axis O—O along the X axis, and increasing through steps of 0, $\pi/2$, $\pi$, and $3\pi/2$ going away from the optical axis O—O along the y axis. At the design wavelengths, these components operate mainly at order $p=+1$ in the X direction and $p=-1$ in the Y direction, and they provide the same correction powers in the X and Y directions respectively as the components shown in FIGS. 10A and 10B:

$+1/f_x=+2\lambda/\Delta r_x^2$ $+1/f_y=-2\lambda/\Delta r_y^2$

Lenses equipped with diffractive components having the phase profiles shown in FIGS. 12A and 12B therefore correct the same ametropia as the lenses shown in FIGS. 10A and 10B.

In FIGS. 13A and 13B, the phase profiles of the hyperbolic-outline diffractive components are of the binary type, comprising two subzones with a phase difference of $\pi$, more precisely, for each diffractive structures, there is a $\pi$ phase shift zone close to the optical axis O—O of the lens and a zone of 0 phase shift at a distance along the X axis from the optical axis O—O, whereas there is a zone of 0 phase shift close to the optical axis O—O of the lens and a zone of phase shift $\pi$ at a distance along the Y-axis from the optical axis O—O. These components operate simultaneously at order $p=+1$ and at order $p=-1$.

At order $p=+1$, the diffractive components provide the following correction power along the X and Y directions respectively:

$+1/f_x=+2\lambda/\Delta r_x^2$ $+/b \ 1/f_y=+2\lambda/\Delta r_y^2$

At order $p=-1$, the diffractive components provide the following correction powers along the X and Y directions respectively:

$+1/f_x=-2\lambda/\Delta r_x^2$; and $+1/f_y=-2\lambda/\Delta r_y^2$

Lenses fitted with diffractive components having phase profiles as shown in FIGS. 13A and 13B may be used for four types of correction, corresponding to those of the lenses shown in FIGS. 7A and 7B, as described above.

In FIGS. 14A and 14B, the phase profiles of the hyperbolic-outline diffractive components are of the binary type comprising two subzones at a phase difference of $\pi$, and more precisely, for each diffractive structure, there is a zone of 0 phase shift close to the optical axis O—O of the lens and a zone of $\pi$ phase shift at a distance in the X direction from the optical axis O—O, whereas there is a zone of $\pi$ phase shift close to the optical axis O—O of the lens and a zone of 0 phase shift at a distance in the Y direction from the optical axis O—O.

These components have exactly the same correction powers at orders $+1$ and $-1$ as the components shown in FIGS. 13A and 13B.

FIGS. 15A and 15B show the phase profiles of a special hyperbolic component whose periodicity is identical along both the X axis and the Y axis.

Regardless of the phase profiled chosen (it is of the pure kinoform type in FIGS. 15A and 15B, but it could equally well have been of the sampled kinoform type or of the type having a 0, $\pi$ squarewave function binary profile), the focal lengths in the X and Y directions always have the same absolute vale when using a grid of equilateral hyperbolas.

Naturally, a diffractive lens including a hyperbolic type of diffractive component may have additional refractive power associated therewith obtained by the geometry of the lens in order to bring both of the focal lengths $f_x$ and $f_y$ into the desired correction region.

Diffusion examples of corrections obtained using hyperbolic-outline diffractive components are now described.

EXAMPLE 4

A correction of $-2d$ with an astigmatic correction of $+3d$ (X axis cylinder) may be obtained without additional refractive power by using a lens of the type shown in FIGS. 9A and 9B or of the type shown in FIGS. 11A and 11B, providing a diffractive power $P_x = -2d$ on the X axis and a diffractive power $P_y = +1d$ on the Y axis, i.e. with a radial variation law $$r_{Kx} = \sqrt{2k\lambda|f_x|} = 0.74\sqrt{k} \text{ mm and}$$

$$r_{Ky} = \sqrt{2k\lambda|f_y|} = 1.04\sqrt{k} \text{ mm.}$$

EXAMPLE 5

A correction of $-1d$ with an astigmatic correction of $+3d$ (Y axis cylinder) may be obtained without additional refractive power using a lens of the type shown in FIGS. 10A and 10B or of the type shown in FIG. 12A and 12B, generating a diffractive power $P_x = +2d$ on the X axis and a diffractive power $P_y = -1d$ on the Y axis, i.e. in accordance with a radial variation law $$r_{Kx} = \sqrt{2k\lambda|f_x|} = 0.74\sqrt{k} \text{ mm and}$$

$$r_{Ky} = \sqrt{2k\lambda|f_y|} = 1.04\sqrt{k} \text{ mm.}$$

EXAMPLE 6

Diffractive components whose phase profiles are as shown in FIGS. 13A and 13B and FIGS. 14A and 14B have exactly the same correction powers and may be used for both types of correction mentioned above in Examples 4 and 5 using the same radial variation law $$r_{Kx} = \sqrt{2k\lambda|f_x|} = 0.74\sqrt{k} \text{ mm and}$$

$$r_{Ky} = \sqrt{2k\lambda|f_y|} = 1.04\sqrt{k} \text{ mm.}$$

Components in accordance with FIGS. 13A and 13B and with FIGS. 14A and 14B provide a basic correction of $-2d$ and an astigmatic correction of $+3d$ (X axis cylinder) at order $p = -1$ for X and $p = +1$ for Y.

The same components as shown in FIGS. 13A and 13B and FIGS. 14A and 14B, provide a basic correction of $-1d$ and an astigmatic correction of $+3d$ (Y axis cylinder) at order $p = +1$ for X and $p = -1$ for Y.

It is essential to observe that when using a pure or sampled kinoform type hyperbolic-outline component, the powers along the X and Y axes are always opposite in sign.

Consequently, it is not possible to obtain same-sign powers in the X and Y directions for a lens making use solely of a pure or sampled kinoform type hyperbolic-outline diffractive component.

If same-sign lens powers are required, then the lens with which said component is associated must be provided with refractive power, as shown in Example 7 below.

EXAMPLE 7

A correction of $-4d$ with an astigmatic correction of $+2d$ (Y axis cylinder) may be obtained by using an additional refractive power of $-3d$, using a hyperbolic type contact lens having $\Delta r_x^2 = \Delta r_y^2$ with a pure type kinoform profile as shown in FIGS. 15A and 15B generating a diffractive power $P_x = +1d$ on the X axis and a diffractive power $P_y = -1d$ on the Y axis i.e.

$$r_{Kx} = \sqrt{2k\lambda|f_x|} = 1.04\sqrt{k} \text{ mm and}$$

$$r_{Ky} = \sqrt{2k\lambda|f_y|} = 1.04\sqrt{k} \text{ mm.}$$

The diffractive components of the present invention are preferably formed by index variation, although it is theoretically possible for such components also to be obtained in relief, for example.

It may also be observed that it is necessary to orient the diffractive component relative to the horizontal and vertical axes of the lens.

The astigmatism of a person's eye is rarely oriented at 0 degrees (horizontal axis) or at 90 degrees (vertical axis) but generally lies on an axis distinct from the two reference axes.

Further, a contact lens for correcting astigmatism must be angularly oriented on the eye in a manner which is accurately defined and which is stable, i.e. it must not be subject to rotation about its own axis, e.g. due to movement of the eyelids, and in particular of the top eyelid.

For this reason, astigmatic contact lenses of the invention should include means for stabilizing their orientation on the eye. These means may be selected from the group comprising:

a ballast prism as taught in patent document EP-A-0 008 726;

a horizontal truncation at the bottom portion of the lens;

reduced-weight top and bottom zones (i.e. thinned zones);

a toroidal outer zone as taught in patent document FR-A-2 425 088; or else one or more bulges placed on the horizontal stabilization axis as taught in patent document EP-A-0 042 023.

Naturally, the present invention is not limited to the particular embodiments described above but extends to any variants in accordance with the spirit thereof.

What is claimed is:

1. A lens for correcting astigmatism, including adjacent hyperbolic- or elliptical-outline diffractive components whose periodicity in two mutually orthogonal X and Y directions intersecting at the axis of the lens and coinciding with the main axes of the hyperbolas or the ellipses are respectively determined by the equations:

$$\Delta r_x^2 = 2\lambda|f_x|; \text{ and}$$

$$\Delta r_y^2 = 2\lambda|f_y|;$$

in which:

$\Delta r_x^2$ represents the periodicity in $r^2$ along the X direction;

$\Delta r_y^2$ represents the periodicity in $r^2$ along the Y direction;

$\lambda$ represents the means utilization wavelength;

$f_x$ represents the desired focal length in the X direction; and $f_y$ represents the desired focal length in the Y direction.

2. A lens according to claim 1, wherein the diffractive components have elliptical outlines defined by the equation:

$$x^2/|f_x| + y^2/|f_y| = 2\lambda k$$

where k represents an integer.

3. A lens according to claim 1, wherein the diffractive components have hyperbolic outlines defined by the equations:

$$x^2/|f_x| - y^2/|f_y| = 2\lambda k; \text{ and}$$

$$y^2/|f_y| - x^2/|f_x| = 2\lambda k$$

in which k represents an integer.

4. A lens according to claim 1, wherein the diffractive components are made by index variation.

5. A lens according to claim 1, wherein the diffractive components have a pure kinoform type phase profile varying between 0 and $2\pi$.

6. A lens according to claim 1, wherein the diffractive components have a sampled kinform type phase profile comprising n subzones at phase differences of $2\pi/n$.

7. A lens according to claim 1, wherein the diffractive components have a binary phase profile comprising two subzones at a phase difference of $\pi$.

* * * * *

UNITED STATES PATENT AND TRADEMARK OFFICE
CERTIFICATE OF CORRECTION

PATENT NO. : 5,016,977

DATED : May 21, 1991

INVENTOR(S) : Baude et al.

It is certified that error appears in the above-identified patent and that said Letters Patent is hereby corrected as shown below:

On the title page:
[73] Assignee delete "Essilor International-Compagnie Generale"
           insert --Essilor International-Compagnie Generale d'Optique--

| | | |
|---|---|---|
| [57] Abstract, line 08 | delete "x and y" | insert --X and Y-- |
| [57] Abstract, line 12 | delete "x" | insert --X-- |
| [57] Abstract, line 14 | delete "y" | insert --Y-- |
| col. 03, line 30 | delete "being" | insert --having-- |
| col. 03, line 35 | delete "given" | insert --plan-- |
| col. 05, line 38 | delete "p +" | insert --p = -- |
| col. 05, line 47 | delete "zones" | insert --zone-- |
| col. 05, line 57 | delete "+1/fx = +2$\lambda/\Delta r_x$ ;" | insert --+1/$f_x$ = +2$\lambda/\Delta r_x^2$;-- |
| col. 06, line 22 | delete "in" | insert --is-- |
| col. 06, line 29 | delete "p = =1" | insert --p = +1-- |
| col. 08, line 55 | delete "form" | insert --from-- |
| col. 09, line 61 | delete "y" | insert --Y-- |

UNITED STATES PATENT AND TRADEMARK OFFICE
CERTIFICATE OF CORRECTION

PATENT NO. : 5,016,977

DATED : May 21, 1991

INVENTOR(S) : Baude et al.

It is certified that error appears in the above-identified patent and that said Letters Patent is hereby corrected as shown below:

col. 10, line 25     delete "+/b $1/f_y = +2\lambda/\Delta r_\gamma^2$"     insert --$+1/f_y = +2\lambda/\Delta r_\gamma^2$-- col. 10, line 62     delete "vale"     insert --value-- col. 11, line 01     delete "Diffusion"     insert --Different--

Signed and Sealed this

Twenty-third Day of November, 1993

*Attest:*

BRUCE LEHMAN

*Attesting Officer*     *Commissioner of Patents and Trademarks*